United States Patent [19]
Tyley et al.

[11] 3,992,103
[45] Nov. 16, 1976

[54] DEVICES FOR EVALUATING DROP SYSTEMS

[75] Inventors: Leonard Richard Thomas Tyley, Burnham; Henry Sawistowski, Streatham; Malcolm James Dix, Chiswick, all of England

[73] Assignee: National Research Development Corporation, London, England

[22] Filed: Aug. 4, 1975

[21] Appl. No.: 601,493

Related U.S. Application Data

[63] Continuation-in-part of Ser. No. 436,744, Jan. 25, 1974, abandoned.

[30] Foreign Application Priority Data

Jan. 30, 1973 United Kingdom............... 4500/73

[52] U.S. Cl............................... 356/102; 250/574; 356/103
[51] Int. Cl.$^2$......................................... G01N 15/02
[58] Field of Search ............ 356/37, 102, 103, 104, 356/207; 250/574; 128/DIG. 36

[56] References Cited
UNITED STATES PATENTS 3,609,043  9/1971  Simmons et al. .................... 356/102

OTHER PUBLICATIONS

McCreath et al., "A Technique for Measurement . . . ," *J. Phys. E. Sci. Instrum.* (G. B.) v–5, No. 6, pp. 601–604, June 1972.

*Primary Examiner*—John K. Corbin
*Assistant Examiner*—Matthew W. Koren
*Attorney, Agent, or Firm*—Cushman, Darby & Cushman

[57] ABSTRACT

Apparatus for the analysis of a system of dispersed particulate matter, such as a spray of liquid drops, in which the shadows of the particles are received as a two-dimensional image on a shadow receptor, and the particles lying within a focal plane within the system are focused in a two-dimensional image on to an image receptor, particles not in the focal plane being out-of-focus at the image receptor by a degree dependent on distance from the plane, so that selection of images having a degree of focus greater than a predetermined degree, and therefore having an intensity greater than a predetermined level, allows the analysis of only particles within a known distance of the focal plane.

10 Claims, 4 Drawing Figures

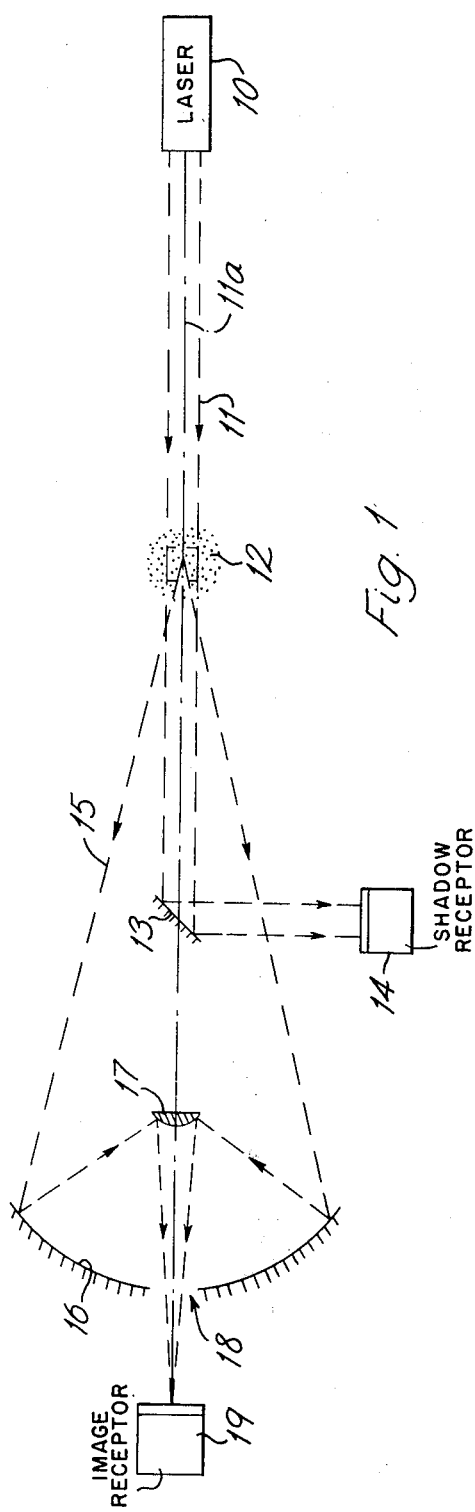
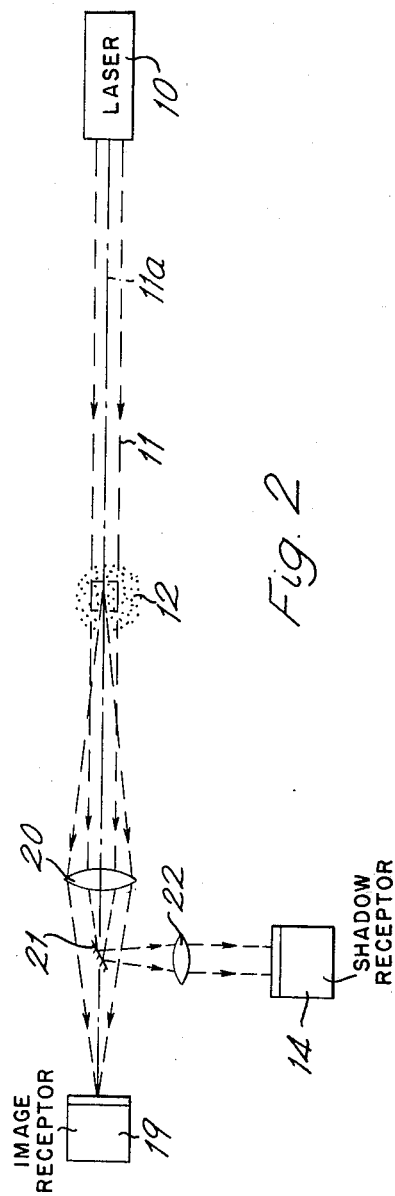

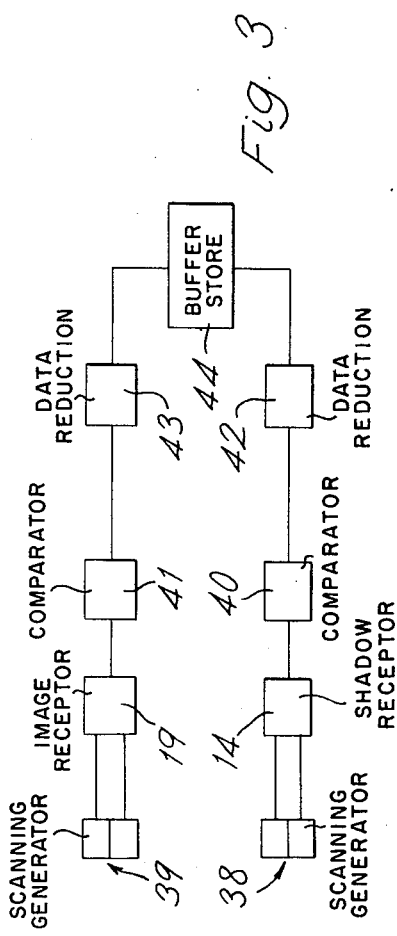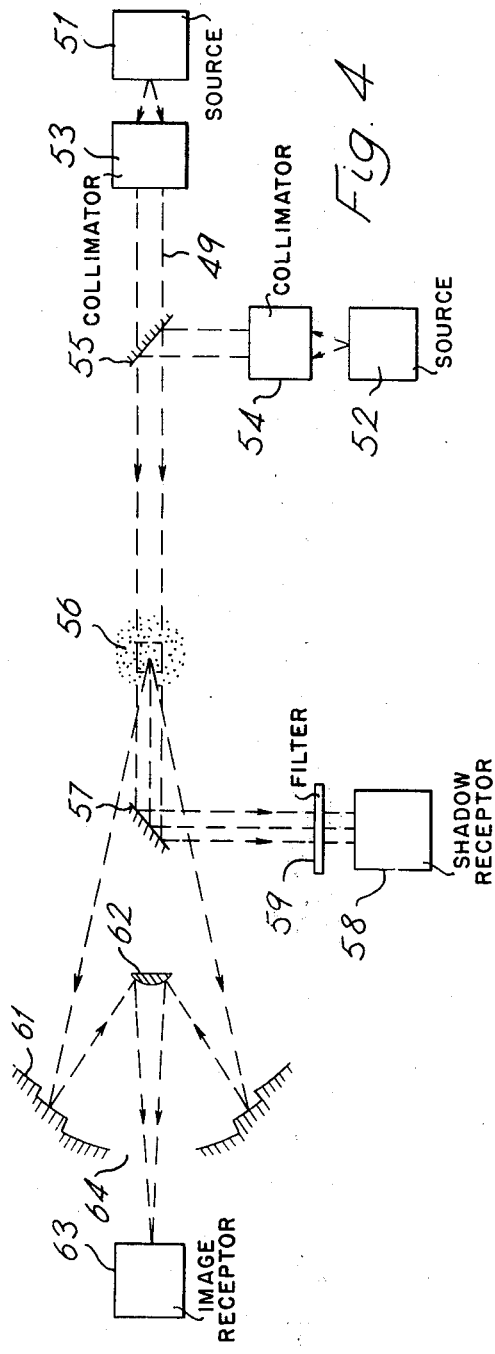

DEVICES FOR EVALUATING DROP SYSTEMS

This application is a continuation-in-part of our co-pending application Ser. No. 436,744 filed Jan. 25, 1974 (now abandoned).

The invention relates to apparatus for use in the analysis of a system of dispersed particulate matter which may be solid or liquid or both.

The possible areas of use of such apparatus cover all processes involving dispersions in the form of sprays or suspensions, and typical examples are spray reactors, spray drying, liquid fuel combustion, agricultural processes, sedimentation and crystallization. In general, the need for particle size measurements arises from development work on dispersing devices, for example atomizers, which should be designed to produce a tailor-made liquid spray, and from the requirements of spray data for process evaluation. Most of the processes in the chemical and allied industries involve chemical reaction as well as interphase heat and mass transfer. For dispersed systems the rate of transfer and the rate of reaction depend critically on the magnitude of interfacial area available so the process cannot be evaluated without a knowledge of particle size distribution.

It is known to measure the size and shape of drops in a spray by recording the spray photographically, then measuring and counting the drops. Velocity in a plane perpendicular to the direction of recording can be obtained by successive photographs recording successive positions of the drops, followed by visual measurement, but the method is laborious and inflexible. While automatic analysis of photographs is possible, such analysis is restricted to records of single-plane drop phenomena and real-time analysis is not possible. It is also known to measure drop size by the introduction into a spray of a sensor in the form of a proximity probe or a charged conductor, etc.; such devices allow real-time analysis, but are unsatisfactory in other ways.

According to the invention, apparatus for use in the analysis of a system of dispersed particulate matter comprises; means for producing a beam of collimated light and directing said beam of light into said system; a first photoresponsive receptor for receiving a first two-dimensional image formed by light from said beam and producing a first signal representing the spatial variations of light intensity in said first image; a second photoresponsive receptor for receiving a second two-dimensional image formed by light from said beam and producing a second signal representing the spatial variations of light intensity in said second image, and optical means for causing said first receptor to receive only light which has passed undeviated through said system and said second receptor to receive only light which has been deviated in passing through said system, said optical means comprising a focusing system disposed in the path of said deviated light.

The invention will now be described by way of example with reference to the accompanying drawings in which:

FIG. 1 illustrates diagrammatically one embodiment of apparatus according to the invention;

FIG. 2 illustrates diagrammatically an embodiment having an optical means different from that shown in FIG. 1;

FIG. 3 illustrates in block diagram form the associated electronic circuitry, and FIG. 4 illustrates diagrammatically another embodiment of the apparatus.

In FIG. 1 a continuous mode laser 10, such as a helium-neon laser or an argon-iron laser, produces a collimated beam of light 11 which is directed along an optical axis 11a to illuminate a spray 12 of liquid drops; it will be initially assumed that all the drops are within a narrow range of sizes. After passage through the spray, light in the beam which has passed undeviated through the spray is reflected by a plane mirror 13 on to a first shuttered image intensifier vidicon which comprises the first photoresponsive receptor, or shadow receptor, 14, the photosensitive screen of this vidicon being disposed perpendicular to the reflection in the mirror 13 of the axis 11a. The shadow receptor effectively receives the shadows of all the drops in the part of the spray through which beam 11 has passed. Thus when scanned appropriately, the vidicon 14 can provide an output signal, the first signal, representing the spatial variations of light intensity in the image it receives, which variations are determined by the size, shape and position of the shadows in a plane perpendicular to axis 11a.

If there are no drops in the part of the spray through which the beam passes, then the shadow receptor is illuminated by all the light in beam 11.

When the beam 11 encounters a drop in the spray 12, the drop deviates the light from the beam, as by refraction and/or scattering, and the deviated light (which effectively forms a divergent beam such as 15) is reflected by a concave mirror 16 on to a convex mirror 17 and through a central aperture 18 in mirror 16 on to a second shuttered image intensifier vidicon which comprises the second photoresponsive receptor, or image receptor, 19, the photosensitive screen of this vidicon being disposed perpendicular to the axis 11a. The mirrors 16, 17 together constitute a focusing system, the curvatures and positions of the mirrors 16, 17 being such that light deviated by the drops in a predetermined plane, which is perpendicular to the axis 11a of the beam and which will be referred to as the focal plane, is focused on to the image receptor as though the drops were point sources. Light deviated by drops on either side of the focal plane is out of focus at the receptor; the drop images increase in size and decrease in intensity as the distance of the drop from the focal plane increases. Thus when scanned appropriately the vidicon 19 can provide an output signal, the second signal, representing the spatial variations of light intensity in the image it receives, which variations are determined by the position and degree of focus of the drop images for drops within a narrow size range. Sharply focused drop images are images of drops in in the focal plane; slightly unfocused drop images are images of drops closely adjacent the focal plane etc.

If there are no drops in the part of the spray through which the beam passes, then the image receptor receives no light from the beam 11.

FIG. 2 shows apparatus having an alternative optical means. A first convex lens 20 is placed on the optical axis 11a so that light deviated by drops lying in a focal plane perpendicular to the axis is focused on to the image receptor 19, and light in the collimated beam which passes undeviated through the spray is focused on to a small mirror 21 which reflects the light through a second convex lens 22 to form a collimated beam which falls on the shadow receptor 14. The same information can be provided as with the apparatus shown in FIG. 1.

In the arrangements of FIGS. 1 and 2, the receptors are exposed to their respective images by simultaneously opening the vidicon shutters for a suitable time interval. If the scanning of the vidicons comprising the two receptors 14 and 19 is appropriately co-ordinated, then correlation of the first and second signals allows the drop images at the image receptor to be matched with the shadows of the same drops at the shadow receptor, provided there are sufficiently few drops to allow unambiguous correlation.

The volume of the spray from which information is obtained is, of course, determined in directions perpendicular to the axis 11a by the cross-section of the beam 11; further, for drops in a narrow size range, this volume is limited in the axial direction by selection only of drop images in or near focus, i.e. drop images from drops within a known, small distance of the focal plane. This can conveniently be achieved by selecting only drop images having an intensity greater than a predetermined level.

Such selection may be made by association with each vidicon of a threshold device which determines which signals are above and below a predetermined level. The device may be set at any level related to the scale-of-grey-related voltage of the vidicon output signal. Such an arrangement is shown in FIG. 3 in which the vidicons 14 and 19 are respectively controlled by staircase function precision scanning generators 38 and 39, the output signals from the vidicons 14 and 19 being respectively applied to voltage comparators 40 and 41, the outputs of which are fed respectively through data reduction means 42 and 43 to a buffer store 44.

An image intensifier vidicon has a long duration image storage capability, and the image on each vidicon can be scanned after the vidicon shutter has been opened then closed. Use of a scanning raster generated by a pair of staircase generators determines that only the voltages at a limited number of positions on the vidicon screen are utilised, the output then being in the form of a matrix; one generator controls the spacing of the matrix points along each line, the other controls line spacing. For example, the screen of each vidicon may be sampled at 100 × 100 equispaced points. The number of matrix points is chosen so that each shadow or image covers several points.

Each element of the vidicon screen provides a voltage $V_1$ directly related to the level of illumination; a second, variable voltage $V_2$ is stored in the voltage comparator which compares the voltages $V_1$ and $V_2$. In the comparator 40 associated with the image receptor, the voltage $V_2$ may be chosen to distinguish signals relating to drop images above the predetermined intensity and therefore corresponding to drops nearer to the focal plane than a predetermined distance. If $V_2$ is comparatively high, then only drops very close to the focal plane will be distinguished; if $V_2$ is set lower, then drops further from the plane will also be distinguished. In the comparator 40 associated with the shadow receptor, the voltage $V_2$ is chosen to eliminate signals caused by stray reflections and optical errors and the setting is not critical; conveniently, it is half the difference between the voltage provided by illumination with all of the beam 11, and the voltage provided when the receptor is screened from beam 11. The comparators thus act as 'threshold' determining means. The voltage comparators provide $V_1 > V_2$ and $V_1 > V_2$ signals in the form of binary 1 or 0 and the signals are passed to the data reduction means.

The signals from the voltage comparator associated with the shadow receptor then represent the size, shape and position of all the drops in the part of the spray through which the collimated beam has passed. The signals from the voltage comparator associated with the image receptor represent the position of only the drops within a predetermined distance of the focal plane. Correlation of the signals allows the drop images to be matched with the shadows of the same drops; signals relating to the shadows of other drops are rejected, allowing the study of the size, shape and position of drops within a known, small distance of the focal plane.

To further reduce the amount of information before feeding it to the buffer store 44, the data reduction means 42, 43 provide information in which only transitions from binary 1 to binary 0 and vice versa (equivalent to transitions from dark to light or light to dark) in each row of the matrix are recorded, together with the co-ordinates of the transition. Signals defining the periphery of each drop shadow and drop image are thus stored. The stored data may be read out on to computer-compatible magnetic or paper tape for ease of calculations using suitable computer programs to provide the required size and position information. Since the method of analysis of the spray drops is likely to be statistical in nature, reduction of the data and computer-compatibility are advantageous. Use of a computer also allows real-time analysis.

A third embodiment of the apparatus is shown in FIG. 4; a light source 51 and collimator 53 provide a collimated beam of light 49 which illuminates a spray 56 through a half-silvered mirror 55. A similar light source 52 and collimator 54 illuminate the spray after reflection by the mirror 55. Light passing undeviated through the spray is reflected by a plane mirror 57 through a filter 59 to a shadow receptor 59, and light deviated by the drops is reflected by the stepped concave mirror 61 and convex mirror 62 to an image receptor 63. The apparatus may be used in conjunction with threshold devices as described with reference to FIG. 3.

Use of a stepped mirror 61 provides a plurality of focal planes in the spray 56; if the steps are of small increments, then the focal plane becomes a focal volume, and drops in that focal volume will be focused on the image receptor, thus increasing the axial length of the spray which can be analysed for the same threshold setting.

Considering use of only one focal plane of the stepped mirror 61, the use of two light sources can provide further information about the spray i.e. the velocity in a plane perpendicular to the axis of beam 49 and speed in the axial direction can be determined. The sources 51, 52 may, for example, be point source flash tubes of different colours or different polarisations, and filter 59 is a colour or polarisation filter chosen to prevent illumination of the shadow receptor 58 by one source. Successive operation of the sources will then provide a single record on the shadow receptor, but will provide two records on the image receptor separated by a known time interval. If there are sufficiently few drops recorded by the image receptor plus threshold means, the successive positions of each drop in directions perpendicular to the axis of beam 49 can be located and the speed of movement calculated. Knowledge of which record was obtained first provides the direction of movement. Speed in the axial direction can also be calculated. Successive drop image pairs may be, for example, (a) first in-focus then out-of-focus, as a drop moves from the focal plane to a position outside that plane; (b) first out-of-focus then in-focus as a drop moves into the focal plane; and (c) both out-of-focus as a drop moves through the plane, or nearer to or further from the focal plane. However, the direction of movement along the axis cannot be determined.

In an alternative mode of operation, the source illuminating the image receptor may be of long duration, so that instead of two records, a single 'streaked' record can be produced; the successive positions of the drops is then linked with minimum ambiguity. Drop images of drops with a component of velocity along the axis will be cone-shaped because the drop image decreases or increases in diameter as a drop respectively approaches or recedes from the focal plane.

Velocity information can also be obtained from the apparatus illustrated in FIGS. 1 and 2 by opening the shutter of vidicon 19 either twice or for a time sufficiently long to provide a 'streaked' record.

The items of apparatus are to some extent interchangeable; for example, the optical means of FIGS. 1 and 2 can be used with the light sources shown in FIG. 4 and vice versa. Another modification if velocity information is not required is the replacement of the continuous mode laser by a single flash mode laser, when the vidicon shutters are superfluous. The image intensifier vidicons may be replaced by other suitable photoresponsive devices such as vidicon tubes. Alternatively each device may be a matrix of photodiodes or a solid state photosensitive matrix or a charge-coupled system; the first and second signals will then be provided in matrix form. Another modification is the incorporation of a macrozoom lens which has the practical advantage of allowing the magnification of the drops to be altered without changing the focal plane.

The invention has been described with reference to a spray of drops which are all within a narrow range of sizes; if drops of considerably differing sizes are present, the intensity of the drop image on the image receptor depends to some extent on the size of the drops, because large drops intercept and deviate more light than small drops.

In general, the magnification of the optical arrangements is chosen to suit the sizes of the drops in the spray and to provide sufficiently few drop shadows and drop images to allow correlation. If, for example, the spray consists of large and small drops, then two sets of measurements may be made at different magnifications and threshold levels which are chosen to allow analysis first of one size then of the other size of drops. Alternatively, if the threshold level is held constant, then the distance from the focal plane at which the large drops are distinguishable is greater than the distance at which the small drops are distinguishable.

We claim:

1. Apparatus for use in the analysis of a system of dispersed particulate matter comprising:
    means for producing a beam of collimated light and directing said beam of light into said system,
    a first photoresponsive receptor for receiving a first two-dimensional image formed by light from said beam and producing a first signal representing the spatial variations of light intensity in said first image,
    a second photoresponsive receptor for receiving a second two-dimensional image formed by light from said beam and producing a second signal representing the spatial variations of light intensity in said second image, and
    optical means for causing said first receptor to receive only light which has passed undeviated through said system and said second receptor to receive only light which has been deviated in passing through said system, said optical means comprising a focusing system disposed in the path of said deviated light.

2. Apparatus as in claim 1 in which said optical means comprises a first lens for focusing deviated light on to the second photoresponsive receptor and for focusing undeviated light on to a plane mirror which reflects light through a second lens on to the first photoresponsive receptor in a collimated beam.

3. Apparatus as in claim 1 in which said optical means comprises a plane mirror for reflecting undeviated light on to the first photoresponsive receptor, and a centrally apertured concave mirror and optically co-operating convex mirror for focusing deviated light on to the second photoresponsive receptor through the aperture in the concave mirror.

4. Apparatus as in claim 3 in which the concave mirror is a stepped mirror.

5. Apparatus as in claim 1 further comprising threshold means associated with the second receptor for detecting when the light intensities in the first and second images are greater than a predetermined variable value.

6. Apparatus as in claim 1 further comprising data reduction means for determining when the light intensity in the first and second images changes between a value greater than and a value smaller than respective first and second predetermined values.

7. Apparatus as in claim 1 in which the means for producing a beam of collimated light and directing said beam of light into said system comprises means for producing a first partial beam of collimated light; means for producing a second partial beam of collimated light, means for directing the first and second partial beams into said system so as to be spatially coincident, the apparatus further comprising filter means for preventing light from one partial beam which has passed undeviated through said system from reaching the first photoresponsive receptor.

8. A method of determining the size and location of particles in a system of dispersed particulate matter comprising:
    directing a beam of collimated light into said system;
    detecting a first two-dimensional image formed by light from said beam passing undeviated through said system and producing a first signal representing the spatial variations of light intensity in said first image;
    detecting a second two-dimensional image formed by light from said beam which has been deviated in passing through said system and which has passed through a focusing system focused on a focal plane perpendicular to the axis of the collimated beam and within said system, and producing a second signal representing the spatial variations of light intensity in said second image,
    selecting from the second signal only those parts relating to light of intensity higher than a predetermined intensity, and correlating said first and said selected second signal to determine the size and position of particles within a predetermined distance of the focal plane.

9. A method as in claim 8 further comprising detecting said second image at two spaced time intervals and producing selected second and third signals representing the spatial variations of light intensity in the second image at said two time intervals, and correlating the first, selected second, and selected third signals to determine the velocity of particles within a predetermined distance of the focal plane in directions parallel to said plane and the speed of said particles in directions parallel to the collimated beam.

10. A method as in claim 8 further comprising detecting the first image for a first time interval, detecting the second image for a substantially longer second time interval, the first and second intervals beginning simultaneously, producing a selected second signal representing the spatial variations of light intensity in the second image during the second time interval, and correlating the first and selected second signals to determine the velocity of particles close to the focal plane in directions parallel to said plane and the speed of said particles in directions parallel to the collimated beam.

* * * * *